United States Patent [19]
Sircar

[11] Patent Number: 4,784,672
[45] Date of Patent: Nov. 15, 1988

[54] REGENERATION OF ADSORBENTS

[75] Inventor: Shivaji Sircar, Wescosville, Pa.

[73] Assignee: Air Products and Chemicals, Inc., Allentown, Pa.

[21] Appl. No.: 107,064

[22] Filed: Oct. 8, 1987

[51] Int. Cl.$^4$ .............................................. B01D 53/04
[52] U.S. Cl. ........................................... 55/26; 55/28; 55/31; 55/33; 55/58; 55/62; 55/68; 55/74; 55/75
[58] Field of Search .................................. 55/26-28, 55/30, 31, 33, 35, 58, 62, 68, 74, 75

[56] References Cited

U.S. PATENT DOCUMENTS

| | | | |
|---|---|---|---|
| 3,109,722 | 11/1963 | Dow | 55/31 X |
| 3,150,942 | 9/1964 | Vasan | 55/31 |
| 3,161,488 | 12/1964 | Eastwood et al. | 55/30 |
| 3,221,476 | 12/1965 | Meyer | 55/31 X |
| 3,479,797 | 11/1969 | Spencer et al. | 55/62 |
| 3,632,504 | 1/1972 | Barrere, Jr. et al. | 55/62 X |
| 3,719,025 | 3/1973 | Heinze et al. | 55/31 |
| 3,738,084 | 6/1973 | Simonet et al. | 55/31 |
| 4,000,990 | 1/1977 | Bingham | 55/30 |
| 4,153,428 | 5/1979 | Saunders et al. | 55/26 |
| 4,233,038 | 11/1980 | Tao | 55/62 X |
| 4,249,915 | 2/1981 | Sircar et al. | 55/26 |
| 4,314,828 | 2/1982 | Saito et al. | 55/31 X |
| 4,324,564 | 4/1982 | Oliker | 55/62 X |
| 4,329,158 | 5/1982 | Sircar | 55/26 |
| 4,636,225 | 1/1987 | Klein et al. | 55/31 |
| 4,711,645 | 12/1987 | Kumar | 55/31 X |

Primary Examiner—Robert Spitzer
Attorney, Agent, or Firm—Geoffrey L. Chase; William F. Marsh; James C. Simmons

[57] ABSTRACT

In the recovery of methane and carbon dioxide from landfill gas (LFG) a selective adsorption system is employed having a pretreat section operated in temperature swing adsorption mode (TSA) to remove water and trace hydrocarbon contaminants, in flow communication with a pressure swing adsorption section (PSA) for separation of the methane from $CO_2$ contained in the purified gas stream discharged from the pretreat section. The LFG is introduced into a column in the TSA section and passed consecutively through a layer of activated carbon followed by a layer of solid desiccant such as a molecular sieve zeolite. The activated carbon layer adsorbs trace contaminants such as hydrocarbons and halohydrocabons boiling above methane; the zeolite layer adsorbs water. Regeneration of the adsorbent layers is carried out by flowing hot regeneration gas first through the zeolite layer then into and through the carbon layer. When the zeolite layer has been heated to the highest regeneration temperature by the regeneration gas, the inlet temperature of the gas is lowered by 100 or more degrees (°F), so that the carbon layer is regenerated at a lower temperature level to avoid detriment to the activated carbon adsorbent that might otherwise occur.

10 Claims, 2 Drawing Sheets

REGENERATION OF ADSORBENTS

TECHNICAL FIELD

The present invention is concerned with an improved method for removal of trace hydrocarbon impurities, water and hydrogen sulfide from a landfill gas prior to its separation to produce high purity methane and carbon dioxide products, particularly with respect to regeneration of the adsorbent utilized in the temperature swing adsorption (TSA) pretreatment cycle for removal of the trace impurities.

BACKGROUND OF THE INVENTION

Landfill gases typically consist of 30–70 mole percent methane in carbon dioxide. They also contain a host of trace hydrocarbon impurities along with water and hydrogen sulfide. These trace impurities need to be removed prior to the bulk separation of methane from carbon dioxide, since these impurities may adversely affect the separation capacity of the selective adsorbent as well as irreversibly destroying the adsorbent employed in the PSA system.

Bingham, U.S. Pat. No. 4,000,990 describes a system comprised of a thermal swing adsorption (TSA) section followed by a pressure swing adsorption (PSA) section for purifying a fluid stream, stated to be applicable in the purification of landfill gas to recover methane. In the TSA pretreat section water and trace amounts of heavier hydrocarbons are removed by adsorption at a superatmospheric pressure and the non-adsorbed effluent is sent to the PSA section wherein $CO_2$ is adsorbed and unadsorbed methane is recovered as product. The TSA section of the patent arrangement is regenerated by passing a heated fluid stream (of void gases) through the adsorbent bed in a closed loop recycle regeneration scheme. The purge effluent is cooled to remove part of the condensible impurities, reheated and recirculated. In the subsequent cooling of the regenerated pretreat column a part of the circulating cool gas is vented. After the bed has been cooled it is repressured to the adsorption pressure with the pretreated gas effluent discharged from a companion pretreater column.

BRIEF SUMMARY OF THE INVENTION

In accordance with the present invention an integrated TSA-PSA process is employed for separation and recovery of substantially pure $CH_4$ and $CO_2$ from a landfill gas composition. The raw gas which contains, in addition to methane and carbon dioxide, a number of a minor impurities including various hydrocarbons boiling above methane as well as minor to trace amounts of halogenated hydrocarbons, is initially subjected to pretreatment for adsorption of minor impurities therefrom and the thus partly purified mixture (consisting essentially of carbon dioxide and methane) is treated in an associated pressure swing adsorption section to separate methane of high purity as non-sorbed effluent, while $CO_2$ is retained in the adsorbent and is recovered as a desorbate during regeneration of the adsorbent. The adsorbent beds in the pretreater columns are regenerated by passing hot through the column in a direction counter to that used for introduction of feed during the adsorption step.

The pretreat column contains at the raw gas feed inlet a layer of adsorbent effective in adsorptive retention of hydrocarbon and halohydrocarbon impurities and approximate the initial discharge end a layer of adsorbent effective in retention of water as well as minor quantities of sulfides and mercaptans. Hot regenerating gas at highest temperature is then introduced to flow through the impurity laden beds in a direction counter to that of the raw gas feed through the clean gas discharge end. When the water-containing section of the column has been heated to such highest temperature, the temperature of the regenerating gas is reduced by several hundred degrees (°F.), whereby the hydrocarbon containing adsorbent is thus regenerated at a significantly lower temperature.

DETAILED DESCRIPTION OF THE INVENTION

Figure 1:
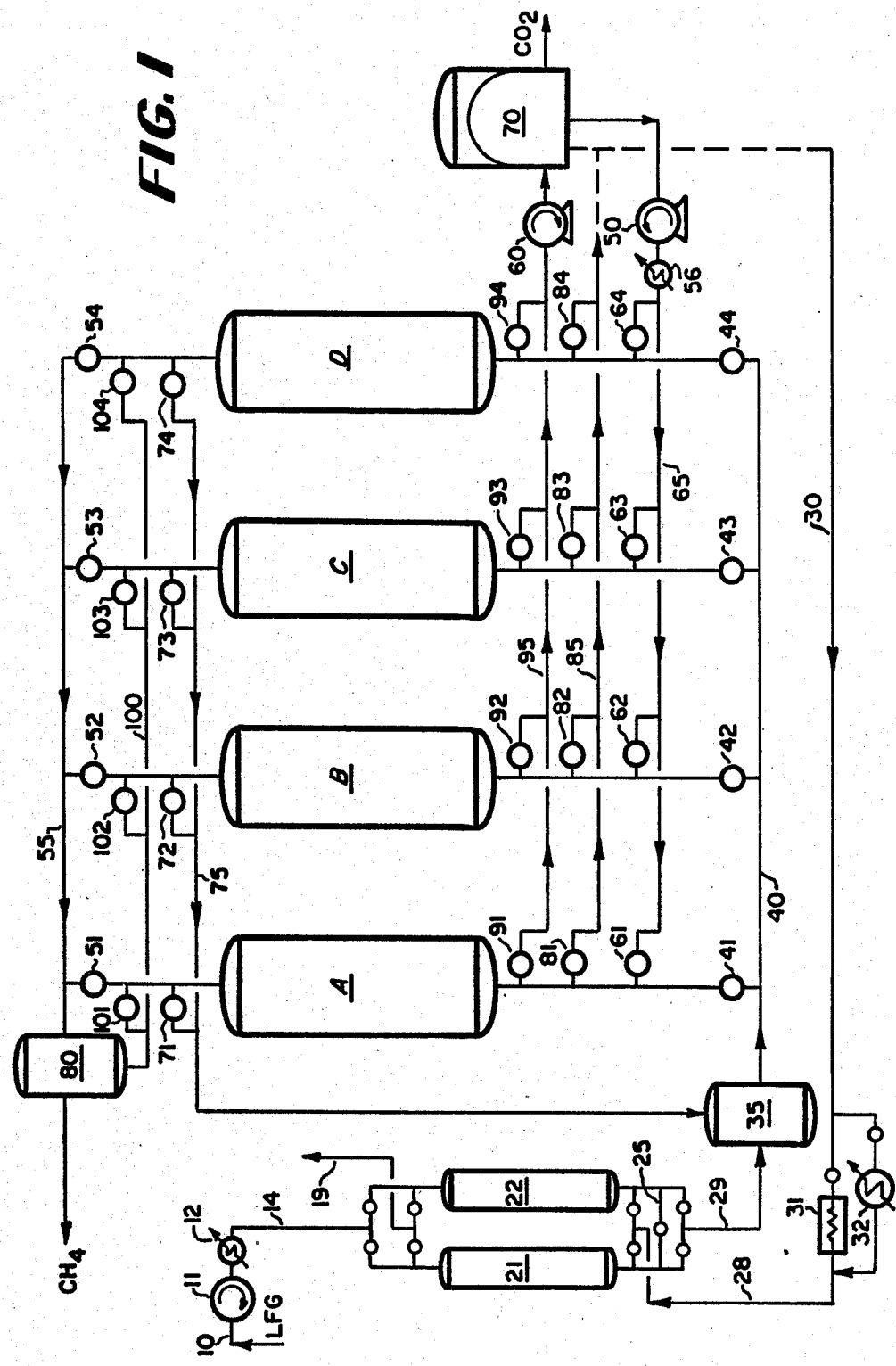
FIG. 1 is a schematic flow diagram of an integrated TSA-PSA system for practice of the invention; and, FIG. 2 is a partial schematic flow diagram of an adsorption column in the pretreat section, showing the direction of gas flow through the adsorbent layers during the adsorption and regeneration steps respectively.

As shown in FIG. 1 of the drawing, the system comprises a multicolumn PSA section comprising adsorbent columns A, B, C, D, operated sequentially in parallel and arranged for gas flow communication therebetween with a two column TSA pretreat section comprising adsorbent columns 21 and 22. The number of adsorbent columns in each of the two sections need not necessarily be that above indicated. Also other combinations and arrangements of PSA and TSA columns may be used in conjunction with the present invention.

The illustrated system further comprises among major components a feed gas compressor 11, aftercooler condenser 12, $CO_2$ compressor 50, vacuum pump 60 and a variable volume constant pressure or constant volume variable pressure storage vessel 70 for product gas ($CO_2$). In addition, high pressure mixing vessels 35 and 80 are provided, to be used as hereinafter explained. The pretreat section as well as the main PSA section are provided with gas flow manifolds and lines connecting these with the individual columns under control of swtiching valves.

The TSA pretreat section is operated in known manner with the following sequence of steps:

(a) Adsorption of water and hydrocarbon and halohydrocarbon impurities from the feed gas; ;hydrogen sulfide and mercaptans, if present, are also adsorbed.

(b) Countercurrent depressuring the adsorption column to ambient pressure level.

(c) Countercurrent thermal regeneration of the impurity laden adsorbent beds in the column at ambient pressure.

(d) Countercurrent cooling the thus regenerated adsorbent beds, and (e) Countercurrent repressuring the cooled column to the designed adsorption pressure.

The cycle time of step (a) is equal to the cycle times for steps (b) through (e) thus allowing continuous flow of cleaned feed to the PSA section.

The PSA section of the illustration is operated in cyclic sequence, each column A–D in turn going through the following sequence of steps:

(1) Selective adsorption of $CO_2$ at super ambient pressure from the pretreated gas which has passed through the adsorbent beds (in 21 or 22), while discharging unadsorbed $CH_4$.

(2) Co-current rinse of the $CO_2$-laden bed at about feed pressure.

(3) Countercurrent depressuring of the rinsed column to near ambient pressure.

(4) Countercurrent evacuation of the column to subatmospheric pressure level.

(5) Countercurrent repressuring of the column using part of the clean $CH_4$ product gas.

Figure 2:
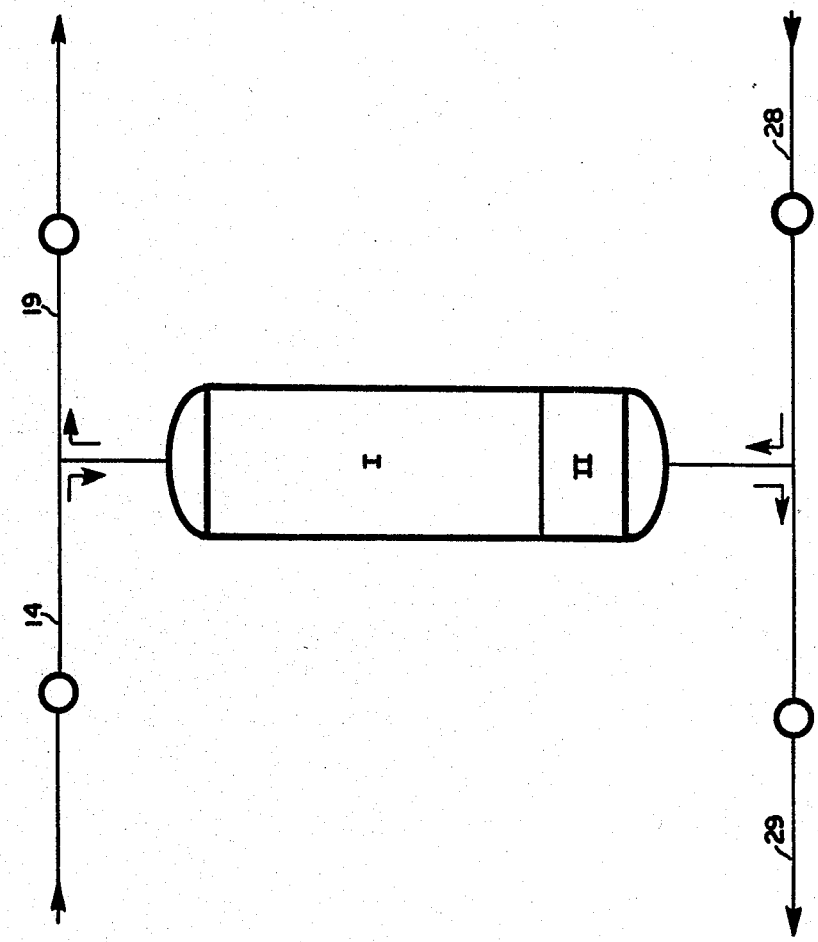

It should be emphasized that the above described PSA cycle for $CO_2$-$CH_4$ separation is for illustration only. Other PSA process schemes which can separate bulk $CO_2$-$CH_4$ mixtures can be used in conjunction with the above described TSA cycle. As illustrated in FIG. 2 of the accompanying drawing each of the columns 21 and 22 contains adsorbent effective in removal of water, sulfur compounds and trace hydrocarbon impurities from a landfill gas (LFG) prior to bulk separation of $CO_2$ from $CH_4$ in the PSA section. The adsorbent is arranged in separate layers I and II respectively at the feed end and product discharge end of the column. The adsorbent employed at the feed end is a layer (I) comprised of activated carbon and that at the discharge end is (II) a layer of an inorganic desiccant such as a zeolite or watersorbing dry gel (silica or alumina) or combinations of these.

Landfill gas typically contains a mixture of 30 to 70% $CH_4$ and 70–30% $CO_2$ besides a large variety of trace hydrocarbon and halohydrocarbon impurities, sulfur compounds as well as residual water which need to be removed before bulk separation of the $CO_2$/$CH_4$ mixture. Table 1 below lists the trace hydrocarbon-type impurities typically occurring in LFG.

TABLE 1

| Typical Raw LFG Impurities | |
|---|---|
| Compound | Conc. (ppm) |
| Pentane | 5 |
| 1,1 dichloroethylene | 1 |
| dichloromethane | 12 |
| 1,2 dichloroethane | 4 |
| 1,1 dichloroethane | 8 |
| Hexane | 28 |
| Benzene | 23 |
| Iso-octane | 4 |
| Trichloroethane | 8 |
| Toluene | 210 |
| Tetrachloroethylene | 35 |
| 1,1,2 trichloroethylene | 0.1 |
| Chlorobenzene | 11 |
| Ethylbenzene | 54 |
| Xylenes | 116 |
| Nonane | 12 |
| Isopropyl benzene | 28 |
| Propyl benzene | 4 |
| Napthalene | 0.1 |
| Hydrogen Sulfide | 0–50 |

Prior to introduction into the TSA section the gas is compressed at 11 to 40 psig or more (preferably to about 95 psig) and cooled to near ambient temperature (~70°–90° F.) in cooler condenser 12, whereby some of the water is condensed and the condensate removed. By further cooling of the compressed gas (to ~40°–45° F.) more water can be removed. It is then introduced into the TSA section (at ~70°–90° F.) to remove remaining water and other contained impurities.

As shown in FIGS. 1 and 2, the compressed and partly dried gas enters the TSA section via line 14 and passes first through the carbon layer (I) where the hydrocarbon (and halohydrocarbon) impurities are selectively adsorbed. Leaving the carbon layer the gas next passes through the desiccant layer (II) where the remaining water is removed together with any sulfur compounds that may be present. The thus cleaned gas leaves the column via line 29.

The TSA column remains on stream in the adsorption stroke for a preset time interval until water or sulfur compounds are about to break through, during which time period substantially all of the other trace impurities will also have been removed. The feed of LFG is now switched to a companion column of the TSA section, while the impurity-laden column is subjected to regeneration.

Regeneration of the impurity-laden column is effected by first depressuring the same to near ambient pressure level by gas withdrawal therefrom via line 19 in a direction countercurrent to that of feed introduction. The column is then heated by passing, in a direction countercurrent to feed direction, a dry impurity-free $CO_2$ gas stream into the column. The regenerating gas stream is preferably one produced in the PSA section, which leaves the PSA section via line 30 (FIG. 1) and is heated at 31. This hot gas, supplied via line 28, is passed through the column at the highest regeneration temperature (400°–600° F.) until an initial contacted portion of the adsorbent in the II layer is heated to about that temperature, at which time the inlet temperature of the hot gas entering the II layer is reduced to a temperature at or below 300° F. (preferably in the range of 200°–300° F.). In so doing, the activated carbon section of the column (I) is regenerated at a significantly lower temperature than that applied to the desiccant layer (II), thus effecting a desired saving in energy over that which would be involved in heating both adsorbent layers in the column to the highest regenerated temperature. The water vapor and desorbed impurities exit the column with the regenerating gas stream via line 19.

Following the heating step effecting desorption of sorbed water and other sorbed impurities, the column is cooled to about ambient temperature (~70°–100° F.) by countercurrent flow of unheated regenerating gas through the column via line 28. This may be done through by-passing heater 31. If cooling to below ambient temperature or at a more rapid rate is desired the gas from line 30 may be cooled as indicated at 32.

Instead of using the carbon dioxide gas stream discharged from the PSA section for heating and/or cooling the TSA column one may employ available nitrogen or air or purified methane or impurity-free LFG for either or both these operations.

When the column has been cooled to about ambient temperature it is brought back to the designed adsorption pressure level by countercurrent introduction, through connecting line 25, of a portion of the dry impurity-free $CO_2$/$CH_4$ mixture produced by the adsorption stroke of a companion pretreatment column, and is ready for repetition of the cycle beginning with the feeding of LFG thereto.

In addition to the energy saved by the TSA regeneration technique employed according to the present invention other valuable benefits achieved include:

(1) As a result of the lower temperature employed in regeneration of the activated carbon adsorbent layer undesirable chemical reactions of the sorbed impurities (such as catalysis, polymerization, etc.) are avoided.

(2) The desorbed hydrocarbon impurities do not flow through the inorganic desiccant layer such as zeolite at the high temperature, so that the destruction of the zeolite (dry gel or other water sorbing material used) by chemical reaction with the hot heavy hydrocarbons is avoided.

(3) During desorption of contained water from the zeolite or gel layer steam is formed which passes into the activated carbon layer and helps desorption of more strongly adsorbed hydrocarbons from the activated carbon. Certain hydrocarbons require steam reactivation for regeneration.

The water-retaining adsorbent layer of the TSA section may be an aluminosilicate molecular sieve zeolite or dried alumina or silica gel or a combination of other material. For the separation of $CO_2/CH_4$ in the PSA section the $CO_2$ retaining adsorbents may be 5A or 13X zeolites, Silicalite, mordenite or activated carbon; 13X zeolite being preferred.

The unadsorbed purified LFG gas leaves column 21 (or 22) of the TSA section through line 29, passing into high pressure mixing vessel 35 from which vessel contained gas is withdrawn for separation in the PSA section. Alternatively line 29 may discharge directly into a column of the PSA section then on the adsorption stroke. The gas discharged through line 19 during regeneration of column 21 or 22 may be vented to the atmosphere or sent to a flare. Both regeneration hot gas as well as the cooling gas is supplied to the column via line 28. The repressuring gas may also be supplied to the TSA section via line 28 or repressuring gas may be supplied from one to the other of columns 21 and 22 through an opened valve in line 25 connecting these columns. The TSA operation can be performed in a four hour cycle, during half of which time period (two hours) each of columns 21 and 22 will be on the adsorption stroke and during the other half of the time on regeneration and repressuring (steps b through e).

While the hot regeneration gas enters column 21 (or 22 in turn) at a temperature in the range of 400° to 600° F. it is cooled by heat exchange with adsorbent layer II which is then at about ambient temperature (70°–90° F.). Thus, the gas passing through adsorbent layer II and into adsorbent layer I will be at a temperature typically in the range of 70° to 120° F., or generally no higher than about 200° F., so that the adsorbent in layer I is not brought to a temperature above 300° F. or a temperature at which damage to the adsorbent or other untoward effect is apt to occur in layer I.

The raw gas that has passed through the pretreat column (21 or 22) is essentially free of water and various minor impurities (such as halogenated hydrocarbons), hydrocarbons boiling above methane and sulfur compounds. The thus pretreated gas consisting essentially of methane and carbon dioxide, is discharged from column 21 (or column 22 in its turn) through line 29 into high pressure mixing vessel 35. Alternatively the purified gas in line 29 may be sent directly to the PSA section, entering one of the columns A, B, C, D then on the adsorption stroke (1).

During a total TSA cycle each of the two columns alternately will be on the adsorption stroke for half the time then on regeneration and repressuring (steps b through e) during the other half of the assigned cycle time. Thus, for an assigned four hour cycle each of the TSA columns will be on the adsorption stroke for two hours, then subjected to (b) depressuring, (c) heating, (d) cooling and (e) repressuring, each of these steps being carried out in 30 minute intervals. Cycle time greater or less than four hours may be employed, depending upon the capacity of the column and the adsorbent employed. Also, if desired, longer time periods may be assigned for the heating and cooling steps than that employed for depressuring and repressuring.

Operation of the PSA section will now be described. The cleaned gas is withdrawn from mixing vessel 35 or directly from line 29 and enters supply manifold 40, from which it can be withdrawn by each of the PSA columns in turn. Assuming that column A is on the adsorption stroke, having been previously brought to designed adsorption pressure level, the gas is passed from manifold 40 into column A through opened valve 41. During passage through the adsorbent bed in that column the $CO_2$ content of the feed gas is selectively adsorbed and an effluent stream of substantially pure methane is discharged through open valve 51 into manifold 55, discharging into storage vessel 80. During the adsorption stroke (1) only valves 41 and 51 associated with column A are in open position. The adsorption stroke is continued until the $CO_2$ level reaches the accepted level tolerated for the high purity $CH_4$ effluent.

At the termination of the adsorption stroke valves 41 and 51 are closed and feed gas flow is switched into one of the other columns of the PSA section. The adsorbent in column A being saturated with sorbed $CO_2$, is now rinsed at the existing superatmospheric pressure with a stream of high purity $CO_2$. This rinse stream is obtained from the storage vessel 70, from which it is withdrawn into manifold 65 after compression at 50 to slightly above feed pressure level and being cooled to about ambient temperature by means 56. The cooled $CO_2$ stream is passed into column A (step 2) through open valve 61. The $CO_2$ rinse gas passes through column A in a direction cocurrent to that of the previous feed gas introduction and is discharged from column A into manifold 75 via open valve 71.

The effluent from column A during the rinsing step has a composition similar to that of the feed gas. It is mixed in vessel 35 with fresh purified feed gas from the TSA section and the mixture charged to a column of the PSA section then on the adsorption stroke. The rinsing of the column is continued for a preset time period during which the adsorbent bed therein is essentially saturated with pure $CO_2$.

At the termination of the rinsing of column A, valves 61 and 71 are closed and valve 81 is opened to depressure the column (step 3) to near ambient pressure level in a direction counter to that of the feed. During this step (3) the previously sorbed high purity $CO_2$ flows out of column A into discharge manifold 85. The gas from manifold 85 may be wholly or partly stored in vessel 70 (as indicated by the dashed line leading to that vessel) or it may be partly rejected. The gas, whether from vessel 70 or directly from line 85, may be used for regeneration of an impurity-laden bed in the TSA section as hereinbefore indicated. Since this gas is comprised of high purity $CO_2$ the non-used part may be collected in vessel 70 as a desired product for use or sale.

When column A is near ambient pressure valve 81 is closed and valve 91 opened to initiate the evacuation of the column (step 4). The residual gas content (high purity $CO_2$) is withdrawn from the column by suction imposed through vacuum pump 60 and passed through line 95 into storage vessel 70. By operation of vacuum pump 60 the column pressure is brought down to about 50–300 torr by gas withdrawal in a direction counter to that of the feed. The part of the high purity $CO_2$ withdrawn by evacuation and not used in regeneration of an adsorbent bed in the TSA section may also be collected as useful product gas.

The rise of the gas storage vessel 70 may be eliminated by proper design of the system so that a part of the desorbed $CO_2$ in step 3 is directly used for rinsing a column undergoing step 2 after the gas is compressed. A part of the desorbed $CO_2$ from step 3 and 4 can similarly be used for regenerating the pretreat columns without the use of the storage vessel 70.

When desired evacuation has been completed valve 91 is closed and valve 101 is opened for initiation of the repressuring step (5). The repressuring is accomplished by withdrawing part of the high purity $CH_4$ from vessel 80 via line 100 and charging the same through opened valve 101 into column A in a direction counter to that of the initial feed, until column A is restored to approximately initial feed pressure level. At the conclusion of the repressuring step the described cycle of operations for the PSA section columns is repeated in the described sequence, each of the PSA columns in turn undergoing the sequence of steps as described for column A. Again vessel 80 may not be needed if the process is appropriately designed.

Table 2 illustrates a time program for the various steps in the sequence based on an embodiment employing a suggested twelve minute cycle for PSA operation and indicating the valve positions during each of the described steps of the sequence. It will be understood, however, that the twelve minute cycle described is merely illustrative and that other time cycles may be employed in practice of the invention, with or without change in the number of adsorption columns utilized.

What is claimed is:

1. In the process for pretreatment of landfill gas by selective adsorption for removal of trace impurities therein prior to bulk separation of $CO_2$ from $CH_4$ contained in the pretreated gas, the improvement which comprises:
 (A) passing said landfill gas at superatmospheric pressure into the feed end and through a column containing successive layers of adsorbent wherein hydrocarbons and halohydrocarbons boiling above methane are removed by selective adsorption in the first of such layers and water and sulfur compound are retained by adsorption in the succeeding layer, thereby producing a purified dry gas effluent discharge at the exit end of said column comprised of substantially purified $CH_4$ and $CO_2$;
 (B) thereafter regenerating the adsorbent layers in said column by the successive steps of:
  (a) depressurizing the column to near ambient pressure level by withdrawal of gas therefrom at its initial feed end;
  (b) passing hot regenerating gas into the column through the initial exit end thereof whereby said gas passes first through said water-retaining adsorbent layer at the highest regeneration temperature until a portion of said layer is heated to said highest regeneration temperature thereby driving off water and impurities earlier sorbed in said layer;
  (c) reducing the inlet temperature of the hot regenerating while continuing passage of the hot gas successively through said water-retaining adsor-

TABLE 2

| | TIME (minutes) | | | | | | | | | | | | | | | |
|---|---|---|---|---|---|---|---|---|---|---|---|---|---|---|---|---|
| COL | 0 to 1.5 | 1.5 to 3.0 | 3.0 to 4.5 | 4.5 to 6.0 | 6.0 to 7.5 | 7.5 to 9.0 | 9.0 to 10.5 | 10.5 to 12.0 | | 0 to 1.5 | 1.5 to 3.0 | 3.0 to 4.5 | 4.5 to 6.0 | 6.0 to 7.5 | 7.5 to 9.0 | 9.0 to 10.5 | 10.5 to 12.0 |
| A | Ad | Ad | R | R | Dp | E | E | Pr | | Ad | Ad | R | R | Dp | E | E | Pr |
| B | E | Pr | Ad | Ad | R | R | Dp | E | | E | Pr | Ad | Ad | R | R | Dp | E |
| C | Dp | E | E | Pr | Ad | Ad | R | R | | Dp | E | E | Pr | Ad | Ad | R | R |
| D | R | R | Dp | E | E | Pr | Ad | Ad | | R | R | Dp | E | E | Pr | Ad | Ad |
| VAL | | | | VALVE POSITION | | | | | | | | | | | | | |
| 41 | O | O | C | C | C | C | C | C | 81 | C | C | C | C | O | C | C | C |
| 42 | C | C | O | O | C | C | C | C | 82 | C | C | C | C | C | C | O | C |
| 43 | C | C | C | C | O | O | C | C | 83 | O | C | C | C | C | C | C | C |
| 44 | C | C | C | C | C | C | O | O | 84 | C | C | O | C | C | C | C | C |
| 51 | O | O | C | C | C | C | C | C | 91 | C | C | C | C | C | O | O | C |
| 52 | C | C | O | O | C | C | C | C | 92 | O | C | C | C | C | C | C | O |
| 53 | C | C | C | C | O | O | C | C | 93 | C | O | O | C | C | C | C | C |
| 54 | C | C | C | C | C | C | O | O | 94 | C | C | C | O | O | C | C | C |
| 61 | C | C | O | O | C | C | C | C | 101 | C | C | C | C | C | C | C | O |
| 62 | C | C | C | C | O | O | C | C | 102 | C | O | C | C | C | C | C | C |
| 63 | C | C | C | C | C | C | O | O | 103 | C | C | C | O | C | C | C | C |
| 64 | O | O | C | C | C | C | C | C | 104 | C | C | C | C | C | O | C | C |
| 71 | C | C | O | O | C | C | C | C | | | | | | | | | |
| 72 | C | C | C | C | O | O | C | C | | | | | | | | | |
| 73 | C | C | C | C | C | C | O | O | | | | | | | | | |
| 74 | O | O | C | C | C | C | C | C | | | | | | | | | |

Ad: Adsorption
R: $CO_2$ Rinse
Dp: Depressuring
E: Evacuation
Pr: Pressuring
O = Open
C = Closed As the adsorbent for removal of $CO_2$ from the gas charged to the PSA section one may employ molecular sieve materials such as 5A or 13X zeolite, silicalite, mordenite or activated carbon; 13X zeolite being preferred. Zeolite adsorbents which have been ion exchanged with one or more metals from groups I and II of the periodic table can also be used.

bent layer and said hydrocarbonladen layer, thereby thermally desorbing the hydrocarbon impurities from the hydrocarbon-laden layer without damage to the adsorbent in said layer;
  (d) cooling the column to about ambient temperature range by flowing unheated gas through the consecutive adsorbent layers; and (e) then restoring the column to the starting superatmospheric pressure level by introduction therein of a stream of purified dry gas comprised of $CH_4$ and $CO_2$.

2. The improvement as defined in claim 1 wherein said recited stream of purified dry gas is that obtained as unsorbed effluent discharged from a companion column then undergoing recited step (A).

3. The method as defined in claim 1 wherein said hot regenerating gas is dry $CO_2$ substantially free of impurities.

4. The method as defined in claim 3 wherein said dry $CO_2$ is that obtained by the bulk separation from its admixture with $CH_4$ in purified landfill gas.

5. The method as defined in claim 1 wherein the initial adsorption of water and trace impurities from the landfill gas is effected at a pressure level in the range of about 3 to 12 atmospheres.

6. The method as defined in claim 1 wherein the hot regenerating gas passed into the column during recited step (b) is at a temperature in the range of about 400° to 600° F.

7. The method as defined in claim 6 wherein the regenerating gas inlet temperature is reduced to a level in the range of 200°–300° F. during recited step (c).

8. The method as defined in claim 1 wherein the regeneration of the water-laden adsorbent layer is carried out at the highest regeneration temperature and the regeneration of the hydrocarbon-laden layer is carried out a lower temperature not exceeding 300° F.

9. The method as defined in claim 1 wherein the hot regenerating gas is air or nitrogen or methane or impurity-free landfill gas.

10. The method as defined in claim 1 wherein the unheated regenerating gas employed in cooling step (d) is air or nitrogen, methane or impurity-free landfill gas.

* * * * *